(12) United States Patent
Jung et al.

(10) Patent No.: US 9,593,018 B2
(45) Date of Patent: Mar. 14, 2017

(54) CARBON NANOTUBE COMPOSITE AND METHOD OF MANUFACTURING THE SAME

(71) Applicant: Korea Institute of Science and Technology, Seoul (KR)

(72) Inventors: Yong Chae Jung, Wanju-gu (KR); Sang Hyun Lee, Wanju-gun (KR); Min Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 276 days.

(21) Appl. No.: 14/514,608

(22) Filed: Oct. 15, 2014

(65) Prior Publication Data

US 2016/0045644 A1    Feb. 18, 2016

(30) Foreign Application Priority Data

Aug. 18, 2014   (KR) .................. 10-2014-0107214

(51) Int. Cl.
*A61L 31/10*    (2006.01)
*C01B 31/02*    (2006.01)
*G01N 21/80*    (2006.01)

(52) U.S. Cl.
CPC .......... *C01B 31/0253* (2013.01); *G01N 21/80* (2013.01)

(58) Field of Classification Search
None
See application file for complete search history.

(56) References Cited

U.S. PATENT DOCUMENTS

| | | | |
|---|---|---|---|
| 8,394,296 B2 | 3/2013 | Park et al. | |
| 8,778,296 B2 | 7/2014 | Park et al. | |
| 9,147,881 B2 | 9/2015 | Lee et al. | |
| 2009/0203883 A1* | 8/2009 | Cha ..................... | C07K 1/1077 530/350 |
| 2010/0261821 A1* | 10/2010 | Park ..................... | B82Y 30/00 524/186 |
| 2011/0204297 A1* | 8/2011 | Park ..................... | H01B 1/24 252/503 |

FOREIGN PATENT DOCUMENTS

| | | |
|---|---|---|
| KR | 10-2010-0015252 A | 2/2010 |
| KR | 10-2010-0113823 A | 10/2010 |
| KR | 10-2011-0095660 A | 8/2011 |
| KR | 10-2011-0128637 A | 11/2011 |
| KR | 10-1303285 B1 | 9/2013 |
| KR | 10-2014-0027031 A | 3/2014 |

OTHER PUBLICATIONS

Fei, Bin, et al. "Coating carbon nanotubes by spontaneous oxidative polymerization of dopamine." Carbon 46.13 (2008): 1795-1797.
Lee, Minah, et al., "Mussel-inspired functionalization of carbon nanotubes for hydroxyapatite mineralization." Journal of Materials Chemistry 20.40 (2010): 8848-8853.
Saito, Riichiro, et al., "Physical Properties of Carbon Nanotubes." vol. 4 (1998). Downloaded from www.worldscientific.com by Korea Insitute of Science & Technology on Oct. 9, 2014.: v-vii, ix-xii.
Holten-Andersen, Niels, et al., "Protective coatings on extensible biofibres." Nature materials 6.9 (2007): 669-672.
Harrington, Matthew J., et al., "Iron-clad fibers: a metal-based biological strategy for hard flexible coatings." Science 328.5975 (2010): 216-220.
Holten-Andersen, Niels, et al., "pH-induced metal-ligand cross-links inspired by mussel yield self-healing polymer networks with near-covalent elastic moduli." Proceedings of the National Academy of Sciences 108.7 (2011): 2651-2655.
Jung, Yong Chae, et al., "Optically and Biologically Active Mussel Protein-Coated Double-Walled Carbon Nanotubes." Small 7.23 (2011): 3292-3297.

* cited by examiner

*Primary Examiner* — Jake Vu
(74) *Attorney, Agent, or Firm* — NSIP Law (57) ABSTRACT

Provided are a carbon nanotube composite containing a carbon nanotube coated with a protein having a catechol group and a metal ion bound to the catechol group and a method for manufacturing the same. According to the present disclosure, a carbon nanotube composite which exhibits controllable dispersibility and degree of crosslinkage while retaining the intrinsic physical properties of the carbon nanotube may be prepared. Since the phase change and tendency of aggregation of the carbon nanotube composite can be controlled quickly and repeatedly depending on the change in external environment, the carbon nanotube composite may be useful in various industrial fields including medicine, environment, etc. as a self-healing material.

19 Claims, 8 Drawing Sheets

CARBON NANOTUBE COMPOSITE AND METHOD OF MANUFACTURING THE SAME

CROSS-REFERENCE TO RELATED APPLICATION

This application claims priority to Korean Patent Application No. 10-2014-0107214, filed on Aug. 18, 2014, and all the benefits accruing therefrom under 35 U.S.C. §119, the contents of which in its entirety are herein incorporated by reference.

BACKGROUND

1. Field

The present disclosure relates to a carbon nanotube composite and a method for manufacturing the same.

2. Description of the Related Art

A self-healing or self-recovering system refers to a system designed to have the ability to detect such factors as heat, electricity, light, etc. and to recover defects on its own.

Mussel adhesive proteins are typical examples of a naturally occurring self-healing system. The mussel adhesive protein not only has high adhesion property in aqueous environments but also is capable of quickly and stably adhering to fine materials in water, ethanol, oil and organic solvents, thereby exhibiting high dispersion and adhesion properties at the same time.

Carbon nanotube is a cylindrical nanostructure of graphene. Owing to superior physical, chemical, electrical and mechanical properties, it is a useful one-dimensional nanomaterial in various applications and is used as a filler for composite materials, a material for energy storage, or the like.

However, the application of the carbon nanotube in various fields has been limited because of its strong tendency to aggregate, which is characteristic of nanomaterials. To solve this problem, effective control of dispersion and aggregation properties of carbon nanotube using various materials such as mussel adhesive proteins and external factors such as light, solvent, polarity, temperature, pH, etc. is studied.

REFERENCES OF THE RELATED ART

Patent Document

Korean Patent Application Publication No. 10-2010-0015252 (Feb. 19, 2010).

Non-Patent Documents

N. Holten-Andersen, et al., *PNAS* 108, 2651-2655 (2011).
N. Holten-Andersen, et al., *Nat. Mater.* 6, 668-672 (2007)
R. Saito, et al., Physical Properties of Carbon Nanotubes, London (1988).

SUMMARY

The present disclosure is directed to providing a carbon nanotube composite, which exhibits superior dispersibility in a solvent, quickly and repeatedly controllable dispersion and aggregation properties in response to change in external environments and self-healing ability, and a method for manufacturing the same.

The present disclosure is also directed to providing a method for controlling dispersion and aggregation properties of a carbon nanotube composite in response to change in external environments such as pH.

In an aspect, the present disclosure provides a carbon nanotube composite containing: a carbon nanotube coated with a protein having a catechol group; and a metal ion bound to the protein having a catechol group.

In an exemplary embodiment, the protein having a catechol group may be a mussel adhesive protein.

In an exemplary embodiment, the mussel adhesive protein may be coated to a thickness of 2-5 nm.

The carbon nanotube may include at least one selected from a group consisting of a single-walled carbon nanotube, a double-walled carbon nanotube and a multi-walled carbon nanotube.

In an exemplary embodiment, the carbon nanotube coated with the protein having a catechol group may be a dispersible carbon nanotube.

In an exemplary embodiment, the carbon nanotube composite may be in the form of a gel at pH 9.5-10 and in the form of a sol at pH 2-3 in an aqueous solution comprising the carbon nanotube composite.

In an exemplary embodiment, the metal ion may be an $Fe^{3+}$ ion.

In another aspect, the present disclosure provides a method for manufacturing a carbon nanotube composite, including: treating a carbon nanotube with an acid; coating a protein having a catechol group on an outer wall of the acid-treated carbon nanotube; and binding the catechol group with a metal ion by providing a compound containing the metal ion to the carbon nanotube.

In an exemplary embodiment, the acid-treated carbon nanotube may contain a carboxyl group or a hydroxyl group.

In an exemplary embodiment, the protein having a catechol group may be a mussel adhesive protein.

In an exemplary embodiment, said coating the protein having a catechol group on the outer wall of the acid-treated carbon nanotube may include binding a carboxyl group or a hydroxyl group of the acid-treated carbon nanotube to an amine group of the mussel adhesive protein.

In an exemplary embodiment, the protein having a catechol group may be coated along the outer wall of the acid-treated carbon nanotube to a thickness of 2-5 nm.

In an exemplary embodiment, the metal ion may be an $Fe^{3+}$ ion.

In an exemplary embodiment, said binding the catechol group with a metal ion by providing a compound containing the metal ion to the carbon nanotube may further include adjusting pH using an aqueous acid solution and an aqueous base solution.

In an exemplary embodiment, the compound containing the metal ion may be $FeCl_3$.

In an exemplary embodiment, the carbon nanotube composite may be in the form of a gel at pH 9.5-10 and in the form of a sol at pH 2-3 in an aqueous solution comprising the carbon nanotube composite.

In another aspect, the present disclosure provides a method for controlling dispersion and aggregation properties of a carbon nanotube, including: treating a carbon nanotube with an acid; coating a protein having a catechol group on an outer wall of the acid-treated carbon nanotube; forming a carbon nanotube composite by binding the catechol group with a metal ion by providing a compound containing the metal ion to the carbon nanotube; and controlling dispersion and aggregation properties of the carbon nanotube by adjusting the pH of an aqueous solution containing the carbon nanotube composite, wherein the tendency of aggregation of the carbon nanotube increases as pH is increased and the dispersibility of the nanotube increases as pH is decreased.

In an exemplary embodiment, said adjusting the pH may be conducted by adding one or more of an aqueous acid solution and an aqueous base solution to aqueous solution containing the carbon nanotube composite.

The carbon nanotube composite prepared according to the present disclosure can exhibit change in phase and color depending on change in external environment, in particular pH change, and the dispersion and aggregation properties of the carbon nanotube composite can be controlled quickly and repeatedly. Accordingly, the carbon nanotube composite exhibiting phase and color change depending, for example, on pH change may be used to manufacture a biosensor. Also, the carbon nanotube composite exhibiting the controllable dispersion and aggregation properties and self-healing ability may be used as a medical suture for wound sites whose pH condition is changeable. In addition, the carbon nanotube composite may also be industrially used for defect recovery of structural materials.

DETAILED DESCRIPTION

Hereinafter, exemplary embodiments of the present disclosure are described in detail referring to the attached drawings. However, the exemplary embodiments are given for the purpose of illustration of the present disclosure only and the technical idea, constitution and application of the present disclosure are not limited by them.

In the present disclosure, a carbon nanotube refers to a material wherein 6 carbon atoms arranged in a hexagonal shape are connected with each other to form a cylindrical shape.

In the present disclosure, a mussel adhesive protein refers to an adhesive protein derived from mussel, specifically a mussel adhesive protein derived from *Mytilus edulis*, *Mytilus galloprovincialis* or *Mytilus coruscus* or a variant thereof, although not being limited thereto.

In the present disclosure, a carbon nanotube composite refers to a compound wherein at least one carbon nanotube is bound to a metal ion and may include a mono-catechol-metal ion carbon nanotube composite, a bis-catechol-metal ion carbon nanotube composite and/or a tris-catechol-metal ion carbon nanotube composite.

In the present disclosure, a self-healing system or a self-recovering system refers to a system designed to have the ability to detect such factors as heat, electricity, light, etc. and to recover defects on its own without artificial manipulation.

In the present disclosure, a sol refers to a state which retains fluidity, wherein colloidal particles are dispersed in a liquid.

In the present disclosure, a gel refers to a state wherein a sol has lost its fluidity.

In the present disclosure, a mono-catechol-metal ion carbon nanotube composite refers to a composite formed by binding between one metal ion and one catechol group of mussel adhesive protein formed on a carbon nanotube.

In the present disclosure, a bis-catechol-metal ion carbon nanotube composite refers to a composite formed by binding between one metal ion and two catechol groups of mussel adhesive protein formed on two carbon nanotubes.

In the present disclosure, tris-catechol-metal ion carbon nanotube composite refers to a composite formed by binding between one metal ion and three catechol groups of mussel adhesive protein formed on three carbon nanotubes.

Carbon Nanotube Composite

A carbon nanotube composite according to an exemplary embodiment of the present disclosure may contain a carbon nanotube coated with a protein having a catechol group and a metal ion.

Specifically, the carbon nanotube composite may be obtained by reacting the carbon nanotube coated with a protein having a catechol group with a trivalent metal ion such as $Fe^{3+}$.

In an exemplary embodiment, the protein having a catechol group may be a mussel adhesive protein.

The carbon nanotube composite may have superior dispersibility because the protein having a catechol group, e.g., the mussel adhesive protein, is coated on the outer wall of the carbon nanotube. Also, the carbon nanotube composite may exhibit change in binding behavior and phase depending on pH change. That is to say, if the pH of an aqueous buffer solution containing the carbon nanotube composite is 6-7, a mono-catechol-metal ion carbon nanotube composite may be formed. If the pH is 7.5-8, a bis-catechol-metal ion carbon nanotube composite may be formed. And, if the pH is 9-10, a tris-catechol metal ion carbon nanotube composite may be prepared. The change between the mono-, bis- and tris-metal ion carbon nanotube composites may be reversible.

In addition, the carbon nanotube composite may be in the form of a gel as the pH increases and it may be in the form of a sol as the pH decreases.

Accordingly, a carbon nanotube composite which exhibits controllable dispersibility and degree of crosslinkage while retaining the intrinsic physical properties of the carbon nanotube may be prepared. Since the phase change and tendency of aggregation of the carbon nanotube composite can be controlled quickly and repeatedly depending on the change in external environment, the carbon nanotube composite may be useful in various industrial fields as a self-healing material.

Method for Manufacturing Carbon Nanotube Composite

A method for manufacturing a carbon nanotube composite according to an exemplary embodiment of the present disclosure includes: treating a carbon nanotube with an acid; coating a protein having a catechol group on an outer wall of the acid-treated carbon nanotube; and reacting the carbon nanotube with a metal ion.

Each step is described in detail hereinbelow. Although a double-walled carbon nanotube is described as the carbon nanotube for the convenience of illustration, other carbon nanotubes such as a single-walled carbon nanotube, a multi-walled carbon nanotube, etc. may be suitably used in the embodiments of the present disclosure. Also, the carbon nanotube may be used alone or in combination. Also, although a mussel adhesive protein is described as the protein having a catechol group for the convenience of illustration, other proteins having catechol groups other than the mussel adhesive protein may be suitably used in the embodiments of the present disclosure.

Figure 1:
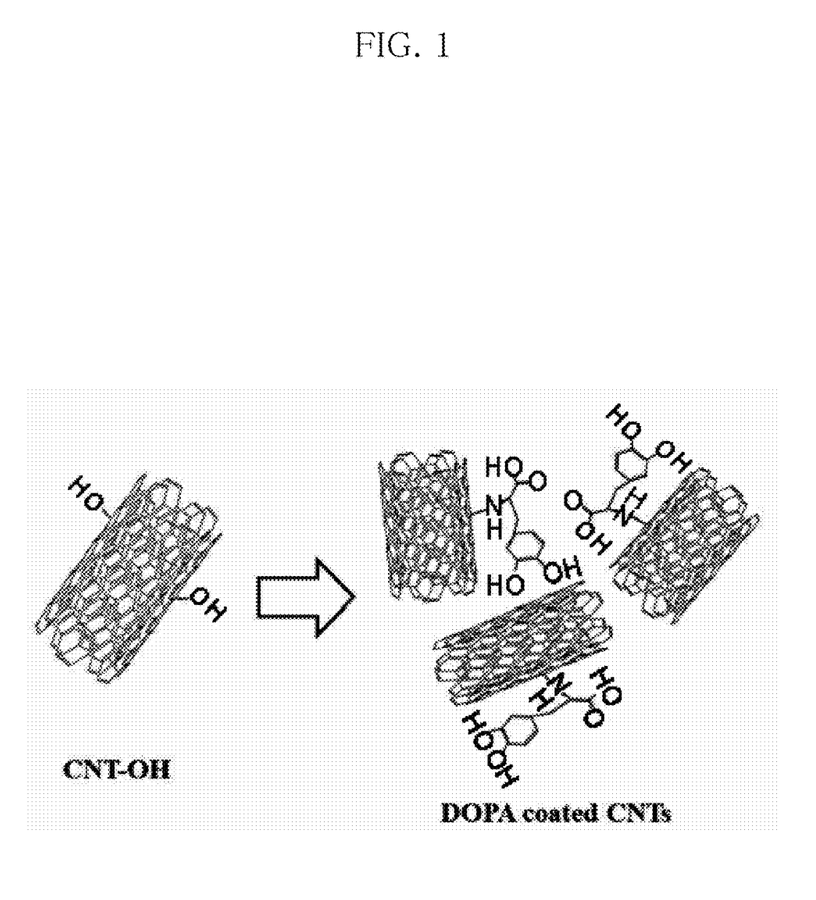
FIG. 1 schematically shows binding between a mussel adhesive protein and a carbon nanotube according to an exemplary embodiment of the present disclosure.

FIG. 1 schematically shows binding between a mussel adhesive protein and a carbon nanotube according to an exemplary embodiment of the present disclosure.

Referring to FIG. 1, a hydroxyl group is formed on an outer wall of a carbon nanotube by treating a carbon nanotube with an acid. Although not shown in the figure, a carboxyl group may be formed instead of the hydroxyl group. For the convenience of illustration, the structure of a mussel adhesive protein is simplified except for the dihydroxyphenylalanine (DOPA) residue.

Then, the mussel adhesive protein and the carbon nanotube are mixed. The hydroxyl group formed on the carbon nanotube may form a bond together with an amine group present on the DOPA residue of the mussel adhesive protein and, as a result, the mussel adhesive protein may be formed along the outer wall of the carbon nanotube.

Figure 2:
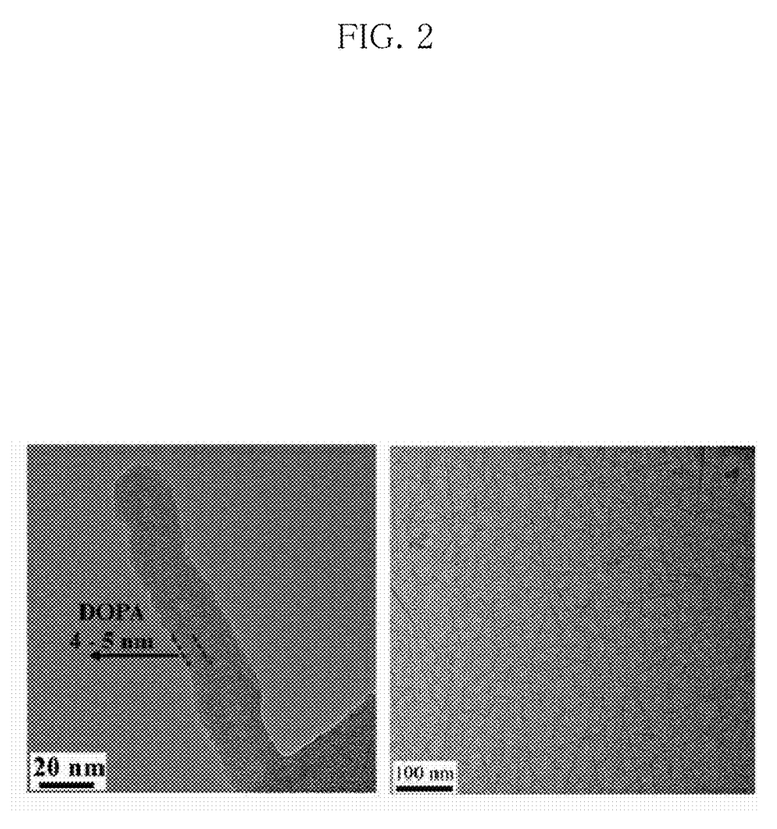
FIG. 2 shows electron microscopic images showing the coating thickness of a carbon nanotube coated with a mussel adhesive protein and the dispersibility of the coated mussel adhesive protein according to an exemplary embodiment of the present disclosure.

FIG. 2 shows images showing the coating thickness of the carbon nanotube coated with the mussel adhesive protein (left) and the dispersibility of the coated mussel adhesive protein (right).

Referring to FIG. 2, the mussel adhesive protein is coated on the carbon nanotube to a thickness of about 2-5 nm, and the carbon nanotube coated with the mussel adhesive protein is uniformly dispersed in an aqueous solution.

Figure 3:
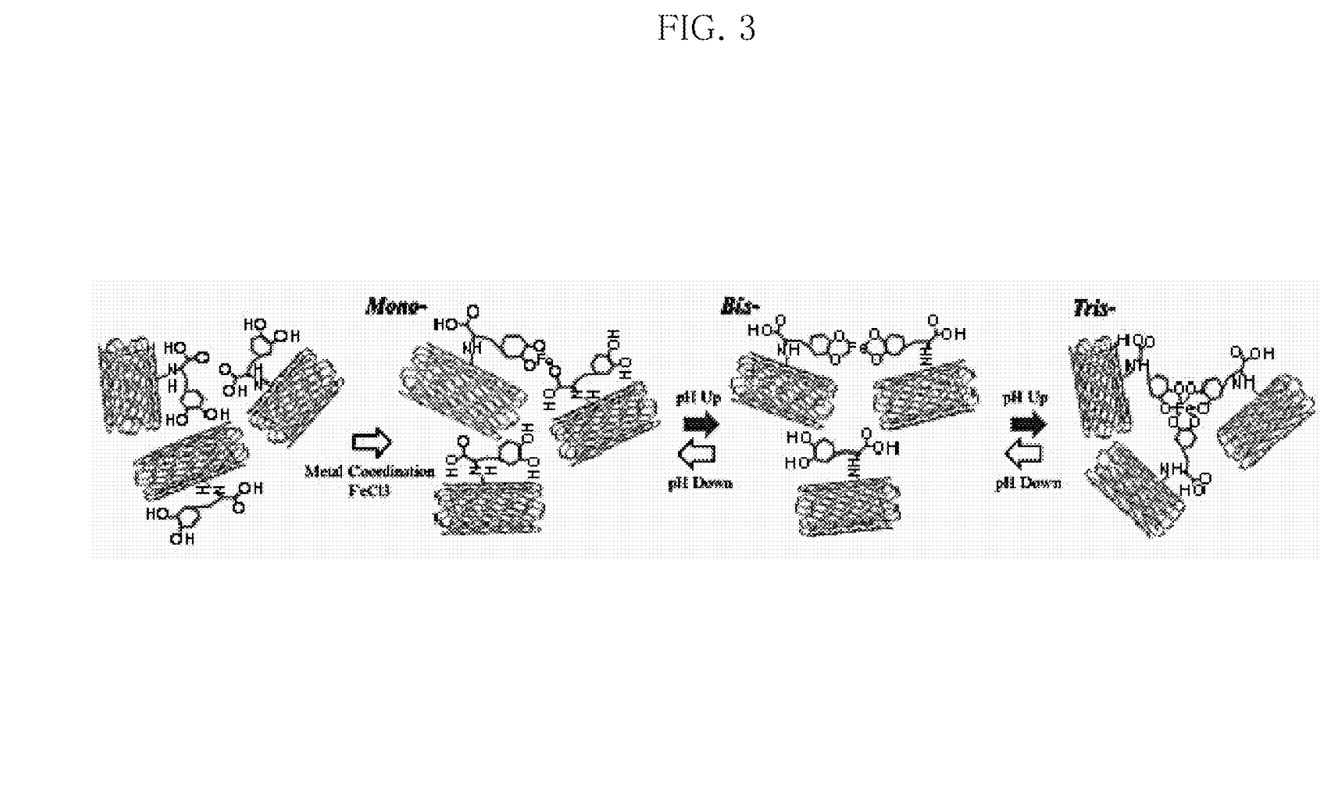
FIG. 3 schematically shows the change in binding of a carbon nanotube composite coated with a mussel adhesive protein according to an exemplary embodiment of the present disclosure depending on pH change.

FIG. 3 schematically shows the formation and the change in binding behavior of the carbon nanotube composite coated with the mussel adhesive protein according to an exemplary embodiment of the present disclosure depending on pH change.

Referring to FIG. 3, the carbon nanotube composite coated with the mussel adhesive protein is dispersed in a buffer solution. Then, a carbon nanotube composite is prepared by reacting the catechol (1,2-dihydroxybenzene) group of the mussel adhesive protein with a metal ion by providing a compound containing the metal ion. In this case, one metal ion may bind to one catechol group of the mussel adhesive protein coated on one carbon nanotube to form a mono-catechol-metal ion carbon nanotube composite.

In an exemplary embodiment, the pH of the buffer solution may be about 7.

In an exemplary embodiment, the compound containing the metal ion may be $FeCl_3$ and the metal ion may be $Fe^{3+}$.

Then, the pH of the solution containing the carbon nanotube composite is changed using a basic aqueous solution and an acidic aqueous solution. Specifically, the pH may be changed to about 7.5-8 by adding a basic aqueous solution. In this case, one metal ion may bind to two catechol groups of the mussel adhesive protein coated on two carbon nanotubes to form a bis-catechol-metal ion carbon nanotube composite.

Subsequently, the pH of the aqueous solution is slowly increased using a basic aqueous solution. If the pH of the aqueous solution is within the range of about 9-10, one metal ion may bind to three catechol groups of the mussel adhesive protein coated on three carbon nanotubes to form a tris-catechol-metal ion carbon nanotube composite. In addition, the carbon nanotube coated with the mussel adhesive protein may exist in the form of a gel due to crosslinkage between the catechol group and the metal ion.

Figure 4:
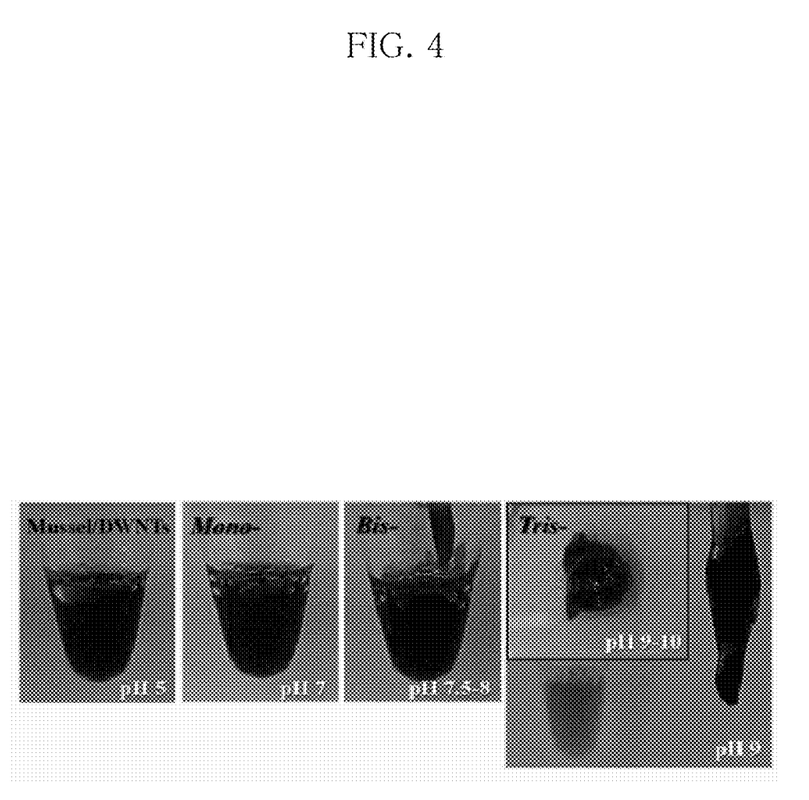
FIG. 4 shows photographic images showing the change in dispersion and aggregation properties of a carbon nanotube composite according to an exemplary embodiment of the present disclosure depending on pH change.

FIG. 4 shows photographic images showing the change in dispersion and aggregation properties of the carbon nanotube composite according to an exemplary embodiment of the present disclosure depending on pH change.

Referring to FIG. 4, it can be seen that the tendency of aggregation of the carbon nanotube composite increased as the pH increases and that the dispersibility of the carbon nanotube composite increased as the pH decreases. Also, it can be seen that the dispersion and aggregation properties of the carbon nanotube composite change reversibly depending on the pH change. Accordingly, the carbon nanotube composite according to the present disclosure can be used as a self-healing material because the phase change and tendency of aggregation can be controlled easily depending on the change in external environment.

Examples

Hereinafter, the present disclosure is being described in further detail through examples. However, the following examples are for illustrative purposes only and it will be apparent to those of ordinary skill in the art that the scope of the present disclosure is not limited by the examples.

(1) Preparation of Carbon Nanotube Coated with Mussel Adhesive Protein 20 mg of a carbon nanotube was added to 80 mL of 30 wt % hydrogen peroxide and sonicated at 4° C. for 2 hours. After filtration, followed by washing with distilled water and drying in a vacuum oven at 60° C. for 24 hours, a carbon nanotube whose outer wall is functionalized with a carboxyl group and a hydroxyl group was obtained. 1 mg of the functionalized carbon nanotube was added to 4 mL of a sodium acetate buffer solution and dispersed by sonicating at 4° C. for 2 hours. The pH of the buffer solution was 5-5.5. After adding 10 mg of a mussel adhesive protein whose molecular weight is 37 kDa to 50 μL of the buffer solution containing the carbon nanotube, the carbon nanotube was coated by binding the carboxyl and/or hydroxyl group on the outer wall of the carbon nanotube with an amine group present in the DOPA group of the mussel adhesive protein through sonication for 2 hours.

(2) Dispersibility of Functionalized Carbon Nanotube Coated with Mussel Adhesive Protein The dispersibility of the carbon nanotube coated with the mussel adhesive protein prepared in (1) was observed with naked eyes and under a transmission electron microscope. As shown in FIG. 2, the carbon nanotube coated with the mussel adhesive protein showed very high dispersibility. In addition, although not shown in the figure, the carbon nanotube coated with the protein remained stable for a long time.

(3) Preparation of Carbon Nanotube Composite

A mono-catechol-metal ion carbon nanotube composite was formed by adding a 100 mM $FeCl_3$ aqueous solution to 1 µL of a 3.6 mM aqueous solution of the carbon nanotube coated with the mussel adhesive protein prepared in (1). Then, a bis-catechol metal ion carbon nanotube composite and a tris-catechol metal ion carbon nanotube composite were formed by adjusting pH using a 5 M NaOH aqueous solution and a 1 M HCl aqueous solution.

Specifically, the mono-catechol-metal ion carbon nanotube composite was formed when the pH of the aqueous solution was 7 and the bis-catechol-metal ion carbon nanotube composite was formed at pH 7.5-8. And, the tris-metal ion carbon nanotube composite was prepared at pH 9-10.

In addition, a secondly formed bis-catechol-metal ion carbon nanotube composite was obtained by lowering the pH of the aqueous solution containing the tris-catechol-metal ion carbon nanotube composite to 7.5-8. Then, a secondly formed mono-catechol-metal ion carbon nanotube composite was obtained by further lowering the pH of the aqueous solution using an acid aqueous solution. Subsequently, a thirdly formed mono-catechol-metal ion carbon nanotube composite was obtained by increasing the pH of the aqueous solution again to 9-10 and then lowering again to 7.

Figure 5:
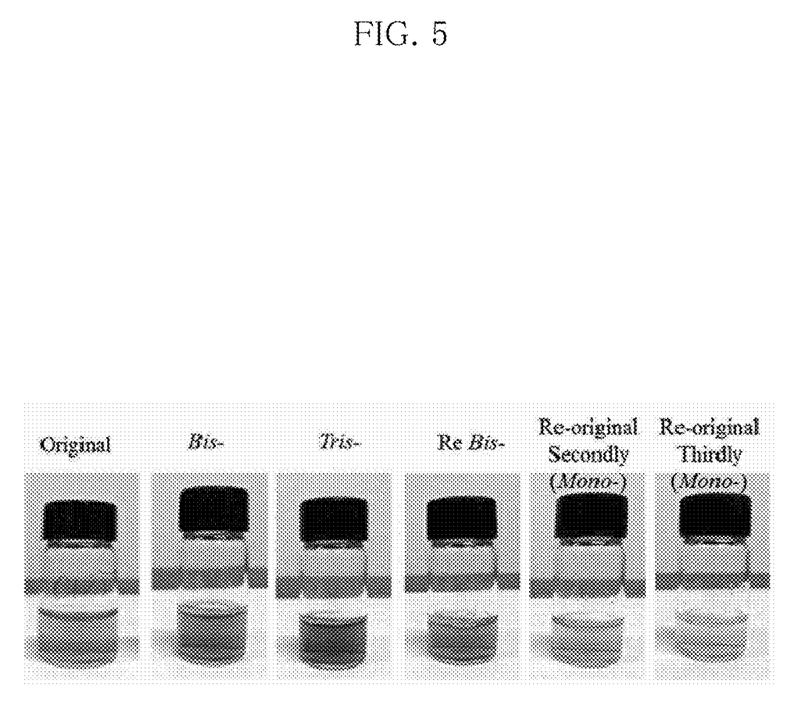
FIG. 5 shows photographic images showing the change in color of a carbon nanotube composite according to an exemplary embodiment of the present disclosure depending on pH change.

(4) Change in Physical Properties of Carbon Nanotube Composite Depending on pH Change The change in color of the carbon nanotube composites obtained through the procedure described in (3) depending on pH change was observed. First, the change in color of the aqueous solutions containing the carbon nanotube composites depending on pH change was measured. The result is shown in Table 1 and FIG. 5.

TABLE 1

| Sample | Color |
| --- | --- |
| Double-walled carbon nanotube coated with mussel adhesive protein | Pale yellow |
| Mono-catechol-metal ion carbon nanotube composite | Pale violet |
| Bis-catechol-metal ion carbon nanotube composite | Dark violet |
| Tris-metal ion carbon nanotube composite | Red |
| Secondly formed bis-catechol-metal ion carbon nanotube composite | Dark violet |
| Secondly formed mono-catechol-metal ion carbon nanotube composite | Pale violet |
| Thirdly formed mono-catechol-metal ion carbon nanotube composite | Pale violet |

The absorption spectra of the carbon nanotube composites obtained through the procedure described in (3) were measured by UV-visible spectrophotometry. The result is shown in FIG. 6.

Figure 6:
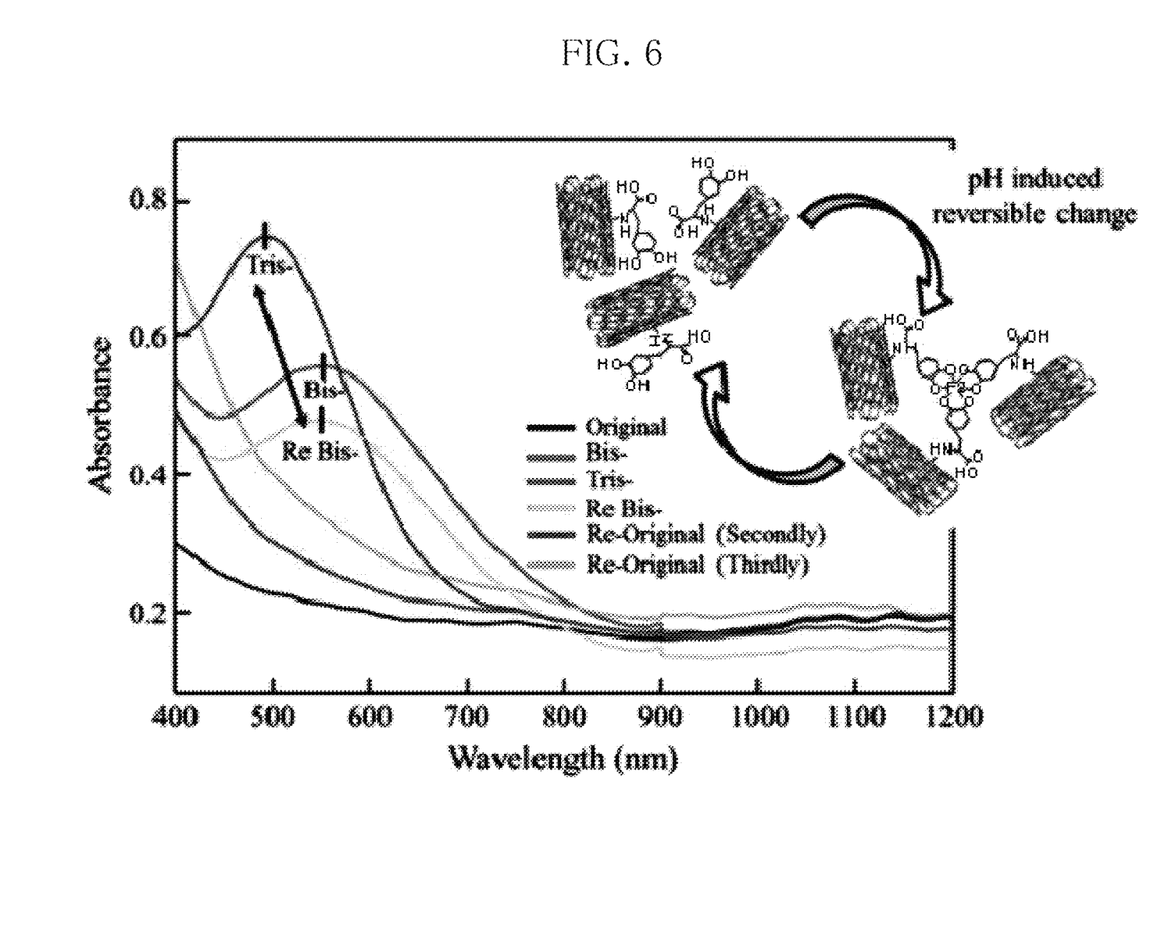
FIG. 6 shows absorption spectra of a carbon nanotube composite according to an exemplary embodiment of the present disclosure depending on pH change.

Referring to FIG. 6, the bis-catechol-metal ion carbon nanotube composite and the tris-catechol-metal ion carbon nanotube composite showed maximum absorption at 560 nm and 493 nm, respectively. And, the maximum absorption of the secondly formed bis-catechol-metal ion carbon nanotube composite was observed around 550 nm. Accordingly, it was confirmed that the physical properties of the carbon nanotube composite are not changed significantly even when the binding between the metal ion and the catechol group in the carbon nanotube composite changes repeatedly depending on pH change.

In addition, the change in physical state from a sol to a gel as the mono-catechol-metal ion carbon nanotube composite is changed to the bis-catechol-metal ion carbon nanotube composite and then to the tris-catechol metal ion carbon nanotube composite was confirmed from the spectra at 900 nm. Likewise, the change in physical state from a gel to a sol as the tris-catechol-metal ion carbon nanotube composite is changed to the bis-catechol-metal ion carbon nanotube composite and then to the mono-catechol metal ion carbon nanotube composite was confirmed from the spectra at 900 nm.

(5) Aggregation and Dispersion Properties of Carbon Nanotube Composite

Figure 7:
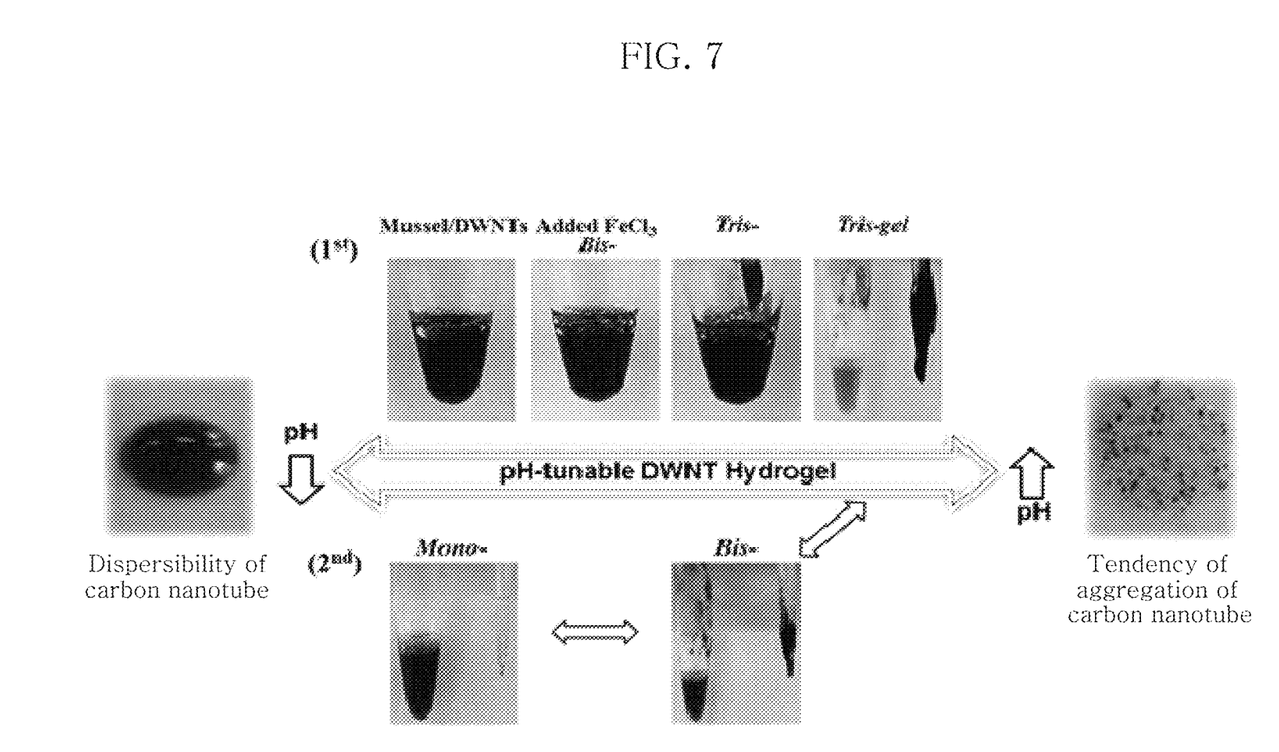
FIG. 7 shows photographic images showing the change in dispersion and aggregation properties of a carbon nanotube composite according to an exemplary embodiment of the present disclosure depending on pH change.

FIG. 7 shows photographic images showing the change in color and dispersion and aggregation properties of the carbon nanotube composite prepared through the procedure described in (3).

Referring to FIG. 7, it can be seen that the tendency of aggregation of the carbon nanotube composite increases as pH increases and that the dispersibility of the carbon nanotube composite increases as pH decreases. In particular, the tendency of aggregation of the tris-catechol-metal ion carbon nanotube composite was superior at high pH. Also, it was confirmed that the dispersion and aggregation properties of the carbon nanotube composite change reversibly depending on pH change.

(6) Self-Recovering Ability of Carbon Nanotube Composite

Figure 8:
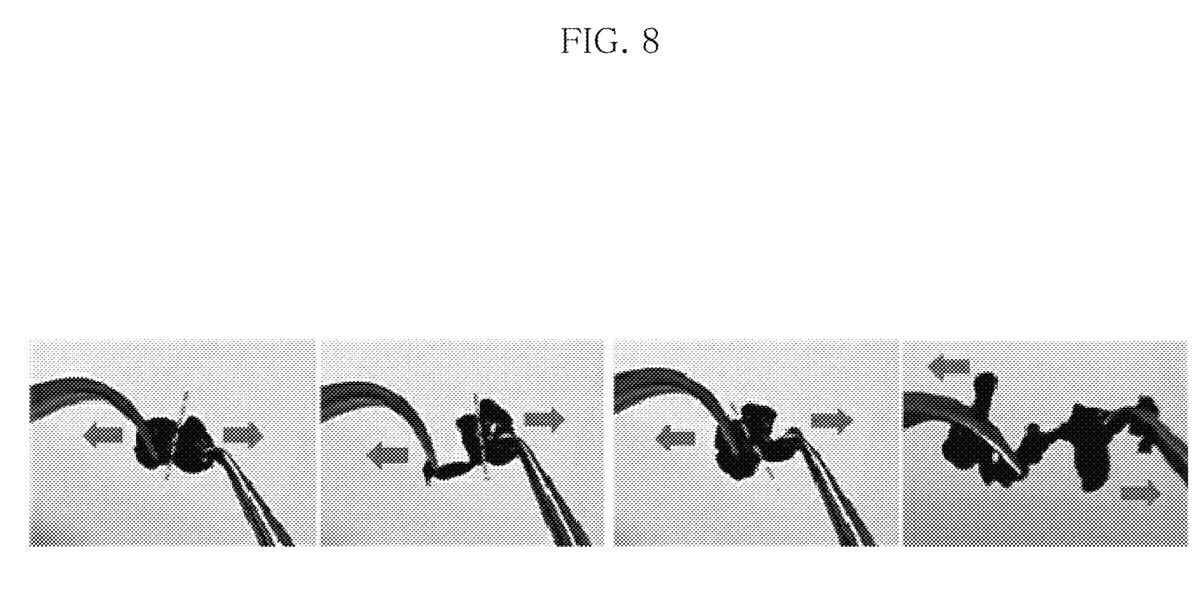
FIG. 8 shows photographic images showing the self-recovering ability of a carbon nanotube composite according to an exemplary embodiment of the present disclosure.

FIG. 8 shows a result of testing the self-recovering ability of the carbon nanotube composite prepared through the procedure described in (3) after repeated cutting. First, the tris-catechol-metal ion carbon nanotube composite in a gel state was cut in half (first cutting). When the carbon nanotube composite was contacted with air, it recovered its original form in less than 60 seconds.

Then, the recovered gel was cut by pulling from both ends (second cutting). The carbon nanotube composite was cut at portions other than those cut during the first cutting. When the carbon nanotube composite was contacted with air, it recovered its original form in less than 60 seconds. It was found out that the portions cut during the first cutting became more rigid as a result of re-bonding and other portions were cut.

Through third cutting followed by self-recovery, fourth cutting followed by self-recovery, etc., it was confirmed that the gel containing the carbon nanotube composite exhibits self-recovering ability after repeated cutting. In addition, when the damaged gel was immersed in an aqueous buffer solution and changed into a sol state by lowering pH and then the carbon nanotube composite was prepared again into a gel state, it also exhibited the self-recovering ability.

What is claimed is:

1. A carbon nanotube composite comprising:
    a carbon nanotube coated with a protein having a catechol group; and
    a metal ion bound to the catechol group.

2. The carbon nanotube composite according to claim 1, wherein the protein having a catechol group is a mussel adhesive protein.

3. The carbon nanotube composite according to claim 1, wherein the protein having a catechol group is coated to a thickness of 2-5 nm.

4. The carbon nanotube composite according to claim 1, wherein the carbon nanotube comprises at least one selected from a group consisting of a single-walled carbon nanotube, a double-walled carbon nanotube and a multi-walled carbon nanotube.

5. The carbon nanotube composite according to claim 1, wherein the carbon nanotube coated with the protein having a catechol group is a dispersible carbon nanotube.

6. The carbon nanotube composite according to claim 1, wherein the carbon nanotube composite is in the form of a gel at pH 9.5-10 and in the form of a sol at pH 2-3 in an aqueous solution comprising the carbon nanotube composite.

7. The carbon nanotube composite according to claim 1, wherein the metal ion is an $Fe^{3+}$ ion.

8. A method for manufacturing a carbon nanotube composite, comprising:
   treating a carbon nanotube with an acid;
   coating a protein having a catechol group on an outer wall of the acid-treated carbon nanotube; and
   binding the catechol group with a metal ion by providing a compound comprising the metal ion to the carbon nanotube.

9. The method for manufacturing a carbon nanotube composite according to claim 8, wherein the acid-treated carbon nanotube comprises a carboxyl group or a hydroxyl group.

10. The method for manufacturing a carbon nanotube composite according to claim 8, wherein the protein having a catechol group is a mussel adhesive protein.

11. The method for manufacturing a carbon nanotube composite according to claim 10, wherein said coating the protein having a catechol group on the outer wall of the acid-treated carbon nanotube comprises binding a carboxyl group or a hydroxyl group of the acid-treated carbon nanotube to an amine group of the mussel adhesive protein.

12. The method for manufacturing a carbon nanotube composite according to claim 8, wherein the protein having a catechol group is coated along the outer wall of the acid-treated carbon nanotube to a thickness of 2-5 nm.

13. The method for manufacturing a carbon nanotube composite according to claim 8, wherein the metal ion is an $Fe^{3+}$ ion.

14. The method for manufacturing a carbon nanotube composite according to claim 8, which further comprises adjusting the pH of an aqueous solution comprising the prepared carbon nanotube composite.

15. The method for manufacturing a carbon nanotube composite according to claim 8, wherein the compound comprising the metal ion is $FeCl_3$.

16. The method for manufacturing a carbon nanotube composite according to claim 8, wherein the carbon nanotube composite is in the form of a gel at pH 9.5-10 and in the form of a sol at pH 2-3 in an aqueous solution comprising the carbon nanotube composite.

17. A method for controlling dispersion and aggregation properties of a carbon nanotube, comprising:
   treating a carbon nanotube with an acid;
   coating a protein having a catechol group on an outer wall of the acid-treated carbon nanotube;
   forming a carbon nanotube composite by binding the catechol group with a metal ion by providing a compound comprising the metal ion to the carbon nanotube; and
   controlling dispersion and aggregation properties of the carbon nanotube by adjusting the pH of an aqueous solution comprising the carbon nanotube composite,
   wherein the tendency of aggregation of the carbon nanotube increases as pH is increased and the dispersibility of the nanotube increases as pH is decreased.

18. The method for controlling dispersion and aggregation properties of a carbon nanotube according to claim 17, wherein said adjusting the pH is conducted by adding one or more of an aqueous acid solution and an aqueous base solution to aqueous solution comprising the carbon nanotube composite.

19. The carbon nanotube composite according to claim 1, wherein an aggregation property of the carbon nanotube composite in an aqueous solution is reversibly responsive to pH.

* * * * *